(12) United States Patent
Bruce et al.

(10) Patent No.: US 8,230,618 B2
(45) Date of Patent: Jul. 31, 2012

(54) ARTICLE OF FOOTWEAR WITH ARCH WRAP

(75) Inventors: Robert M. Bruce, Portland, OR (US); Aaron A. C. Cooper, Portland, OR (US); Bo Lupo, Portland, OR (US); Kurt J. Stockbridge, Lake Oswego, OR (US)

(73) Assignee: NIKE, Inc., Beaverton, OR (US)

( * ) Notice: Subject to any disclaimer, the term of this patent is extended or adjusted under 35 U.S.C. 154(b) by 882 days.

(21) Appl. No.: 12/129,228

(22) Filed: May 29, 2008

(65) Prior Publication Data

US 2009/0293310 A1     Dec. 3, 2009

(51) Int. Cl.
*A43B 5/00* (2006.01)

(52) U.S. Cl. .................. 36/50.1; 36/88; 36/114

(58) Field of Classification Search ........... 36/45, 99, 36/91, 50.1, 88, 114
See application file for complete search history.

(56) References Cited

U.S. PATENT DOCUMENTS

| | | | |
|---|---|---|---|
| 2,052,115 A | 8/1936 | Shulman | |
| 2,473,877 A | 6/1949 | Goldstein | |
| 2,503,586 A | 4/1950 | Miller | |
| 2,530,637 A * | 11/1950 | Taylor | 36/170 |
| 3,308,560 A | 3/1967 | Jones | |
| 4,161,829 A | 7/1979 | Wayser | |
| 4,199,881 A | 4/1980 | Francis | |
| 4,223,455 A | 9/1980 | Vermeulen | |
| 4,231,170 A | 11/1980 | Griswold | |
| 4,342,161 A * | 8/1982 | Schmohl | 36/114 |
| RE31,173 E | 3/1983 | Daswick | |
| 4,447,967 A * | 5/1984 | Zaino | 36/45 |
| 4,553,342 A * | 11/1985 | Derderian et al. | 36/97 |
| 4,622,763 A * | 11/1986 | Adams | 36/50.1 |
| 4,776,111 A * | 10/1988 | Crowley | 36/89 |
| 4,790,048 A | 12/1988 | Arnt | |
| 4,811,500 A * | 3/1989 | Maccano | 36/91 |
| 4,947,560 A * | 8/1990 | Fuerst et al. | 36/88 |
| 5,152,082 A | 10/1992 | Culpepper | |
| 5,319,869 A * | 6/1994 | McDonald et al. | 36/114 |
| 5,371,957 A | 12/1994 | Gaudio | |
| 5,381,614 A | 1/1995 | Goldstein | |
| 5,430,959 A * | 7/1995 | Mitsui | 36/88 |
| 5,491,912 A | 2/1996 | Snabb et al. | |
| 5,692,319 A * | 12/1997 | Parker et al. | 36/50.1 |
| 5,771,608 A | 6/1998 | Peterson | |
| 5,829,169 A * | 11/1998 | James | 36/50.1 |
| 5,940,990 A * | 8/1999 | Barret | 36/55 |
| 5,950,335 A * | 9/1999 | Okajima | 36/115 |
| 6,021,588 A | 2/2000 | Alviso | |
| 6,401,366 B2 | 6/2002 | Foxen et al. | |
| 6,557,271 B1 | 5/2003 | Weaver, III | |
| 6,557,274 B2 | 5/2003 | Litchfield et al. | |
| 6,578,290 B1 | 6/2003 | Meynard | |

(Continued)

OTHER PUBLICATIONS

International Search Report from PCT Application No. PCT/US2009/045275 mailed Aug. 20, 2009.

(Continued)

*Primary Examiner* — Marie Patterson
(74) *Attorney, Agent, or Firm* — Plumsea Law Group, LLC

(57) ABSTRACT

An article of footwear with an arch wrap is disclosed. The arch wrap is configured to provide support to a midfoot. The arch wrap can include a plurality of eyelets that are configured to receive a lace of a lacing system of the upper.

20 Claims, 10 Drawing Sheets

U.S. PATENT DOCUMENTS

| | | |
|---|---|---|
| 6,634,121 B2 | 10/2003 | Sordi |
| 6,658,765 B2 * | 12/2003 | Liu ................................ 36/50.1 |
| 6,671,980 B1 * | 1/2004 | Liu ................................ 36/50.1 |
| 6,691,433 B2 * | 2/2004 | Liu ................................ 36/50.1 |
| 6,785,984 B2 | 9/2004 | Jackinsky |
| 6,912,802 B2 | 7/2005 | Cooper |
| 6,952,890 B1 * | 10/2005 | Blakeslee .................... 36/50.1 |
| D529,691 S | 10/2006 | Earle |
| 7,228,649 B2 | 6/2007 | Elliott |
| 7,249,428 B1 | 7/2007 | Burella |
| 7,287,341 B2 | 10/2007 | Ellis, III |
| 7,290,357 B2 | 11/2007 | McDonald et al. |
| D559,511 S | 1/2008 | Wu |
| 7,325,337 B2 | 2/2008 | Cox et al. |
| 7,337,558 B2 | 3/2008 | Terlizzi et al. |
| 7,543,397 B2 * | 6/2009 | Kilgore et al. ................ 36/50.1 |
| 2002/0166260 A1 * | 11/2002 | Borsoi ........................ 36/50.1 |
| 2003/0014881 A1 | 1/2003 | Hay |
| 2004/0205982 A1 * | 10/2004 | Challe .............................. 36/55 |
| 2004/0255486 A1 * | 12/2004 | Pawlus et al. ...................... 36/10 |
| 2005/0126042 A1 * | 6/2005 | Baier et al. ..................... 36/50.1 |
| 2006/0196079 A1 | 9/2006 | Terlizzi et al. |
| 2007/0119073 A1 | 5/2007 | Brewer et al. |
| 2007/0296115 A1 | 12/2007 | Truelsen |
| 2008/0120871 A1 * | 5/2008 | Sato et al. ......................... 36/88 |

OTHER PUBLICATIONS

Notification Concerning Transmittal of International Preliminary Report on Patentability mailed Dec. 9, 2010 in International Application No. PCT/US2009/045275.

* cited by examiner

ARTICLE OF FOOTWEAR WITH ARCH WRAP

BACKGROUND OF THE INVENTION

1. Field of the Invention

The present invention relates to an article of footwear, and in particular to an article of footwear with an arch wrap.

2. Description of Related Art

Articles with arch wraps have been previously proposed. Weaver (U.S. Pat. No. 6,557,271) teaches a shoe with improved cushioning and support. Weaver teaches an upper portion including a medial longitudinal arch support. The arch support extends from the medial portion of the collar down to a medial side of the calcaneus and talus bones. In addition, the arch support includes a strut or a stabilizing bar that extends down and curves along the medial metatarsal bone and related bones that make up the medial longitudinal arch and, further, turns down and integrates into the lower reinforced sole at a pivot axis of the shoe.

Weaver fails to teach an article with provisions for facilitating tightening of the arch wrap against a foot. There is a need in the art for a design that overcomes these shortcomings.

SUMMARY OF THE INVENTION

The invention discloses an article of footwear with an arch wrap. In one aspect, the invention provides an article of footwear, comprising: an upper; an arch wrap configured to be disposed adjacent to a midfoot of a foot; the arch wrap including an extended portion; and where the extended portion is configured to extend between a toe portion of the upper and an entry hole of the upper.

In another aspect, a lower end portion of the extended portion is disposed proximate to a toe portion of the upper.

In another aspect, an upper end portion of the extended portion is disposed proximate to an entry hole of the upper.

In another aspect, the arch wrap includes two extended portions.

In another aspect, the arch wrap includes a rearward portion disposed adjacent to the lower end portion.

In another aspect, the arch wrap includes a forward portion disposed adjacent to the toe portion of the upper.

In another aspect, the extended portion is disposed at an angle with respect to a lower surface of a sole system of the article of footwear.

In another aspect, the angle has a value in a range between 0 and 90 degrees.

In another aspect, the angle has a value in a range between 30 and 60 degrees.

In another aspect, the invention provides an article of footwear comprising: an upper including a lacing system; an arch wrap configured to be disposed adjacent to a midfoot of a foot; the arch wrap including an extended portion; and where the extended portion is co-extensive with a portion of the lacing system.

In another aspect, the arch wrap extends between a toe portion of the upper and an entry hole of the upper.

In another aspect, the arch wrap includes a first extended portion and a second extended portion.

In another aspect, the first extended portion is partially co-extensive with a medial lacing portion of the lacing system.

In another aspect, the second extended portion is partially co-extensive with a lateral lacing portion of the lacing system.

In another aspect, the invention provides an article of footwear, comprising: an upper including a lacing system; an arch wrap configured to be disposed adjacent to a midfoot of a foot; the arch wrap including an extended portion; and where the extended portion includes a plurality of eyelets that are configured to receive a lace of the lacing system.

In another aspect, the extended portion is co-extensive with a portion of the lacing system.

In another aspect, the lacing system includes a plurality of eyelets.

In another aspect, the plurality of eyelets on the extended portion corresponds to the plurality of eyelets on the lacing system.

In another aspect, the extended portion extends from a toe portion of the upper to an entry hole of the upper.

In another aspect, the extended portion is disposed at an angle with respect to a sole system of the article of footwear.

Other systems, methods, features and advantages of the invention will be, or will become apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

Figure 1:
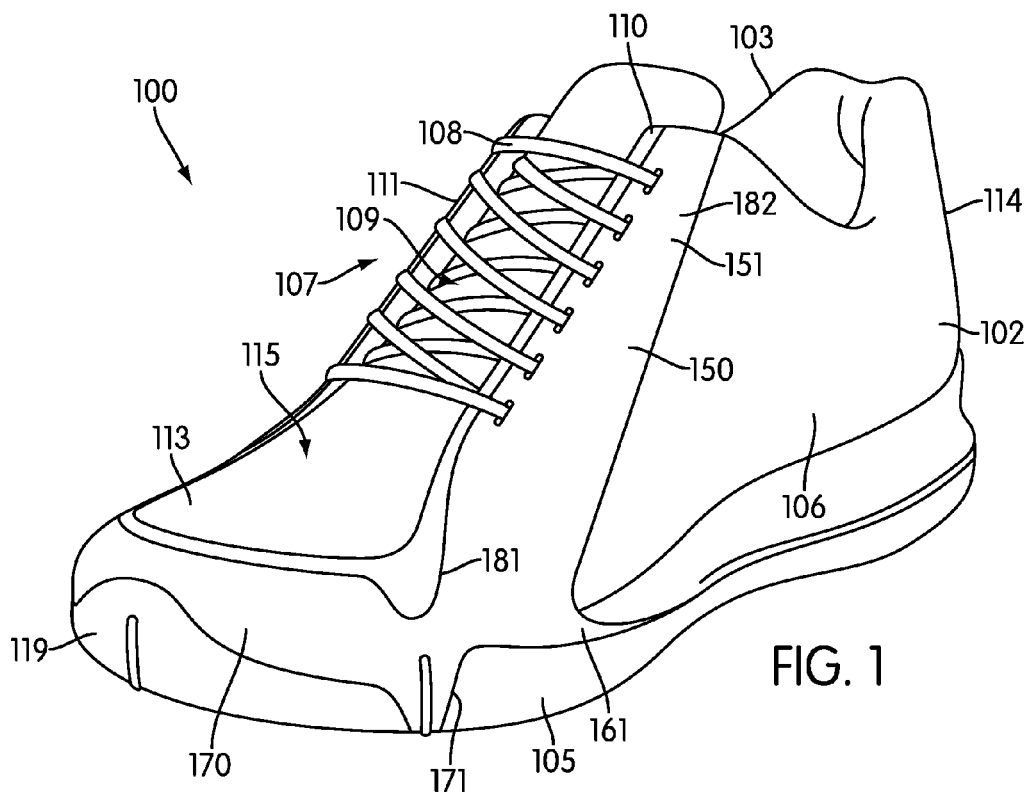
FIG. 1 is an isometric view of a preferred embodiment of a medial portion of an article of footwear.
Figure 2:
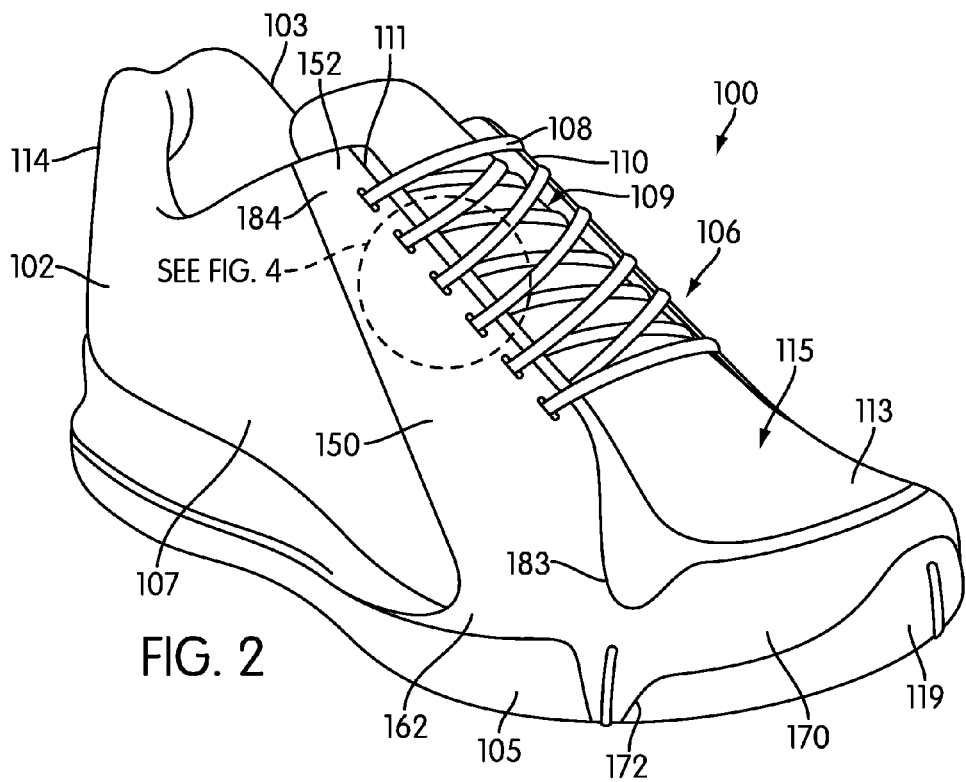
FIG. 2 is an isometric view of a preferred embodiment of a lateral portion of an article of footwear.

FIGS. 1 and 2 illustrate a preferred embodiment of article of footwear 100. In particular, FIG. 1 is an isometric view of a preferred embodiment of a medial portion of article of footwear 100 and FIG. 2 is an isometric view of a preferred embodiment of a lateral portion of article of footwear 100. For clarity, the following detailed description discusses a preferred embodiment, in the form of an athletic shoe or sneaker, but it should be noted that the present invention could take the form of any article of footwear including, but not limited to, soccer shoes, football shoes, rugby shoes, baseball shoes as well as other kinds of shoes. As shown in FIGS. 1 and 2, article of footwear 100, also referred to simply as article 100, is intended to be used with a right foot; however, it should be understood that the following discussion may equally apply to a mirror image of article of footwear 100 that is intended for use with a left foot.

Article of footwear 100 preferably includes upper 102. Generally, upper 102 may be any type of upper. In particular, upper 102 could have any design, shape, size and/or color. For example, in embodiments where upper 102 is a basketball shoe, upper 102 could be a high top upper that is shaped to provide high support on an ankle. In embodiments where upper 102 is a running shoe, upper 102 could be a low top upper.

Preferably, upper 102 is configured to receive a foot of a wearer. In some embodiments, upper 102 includes entry hole 103 configured to receive a foot of a wearer. Typically, entry hole 103 allows a foot to be inserted into an interior of upper 102.

Upper 102 may also include medial portion 106. Also, upper 102 may include lateral portion 107 disposed opposite medial portion 106. Preferably, medial portion 106 may be associated with an inside of a foot. Similarly, lateral portion 107 may be associated with an outside of a foot.

Upper 102 may include toe portion 113 that is associated with the toes of a foot. Also, upper 102 may include heel portion 114 that is associated with a heel of a foot. Upper 102 may also include middle portion 115 that is disposed between toe portion 113 and heel portion 114. Preferably, middle portion 115 is associated with a midfoot, including an arch of the foot and a top of the foot.

In some embodiments, upper 102 may be associated with sole system 105. Sole system 105 may comprise multiple components. In some cases, sole system 105 may include an outsole. In other cases, sole system 105 may include a midsole. In still other cases, sole system 105 may include an insole. In a preferred embodiment, sole system 105 may include an outsole, a midsole and an insole.

In some embodiments, article of footwear 100 may include a fastening system configured to tighten upper 102. Generally, article of footwear 100 could be associated with any type of fastening system including, but not limited to laces, straps, zippers, hook and loop fasteners, as well as other types of fastening systems. In a preferred embodiment, article of footwear 100 includes a fastening system with a lace.

In this embodiment, article of footwear 100 may include lacing system 109. Generally, lacing system 109 may be disposed on any portion of upper 102. In some embodiments, lacing system 109 may be disposed between medial portion 106 and lateral portion 107 of upper 102. In other embodiments, lacing system 109 may be disposed asymmetrically so that a portion of lacing system 109 is disposed entirely within medial portion 106 or lateral portion 107. In a preferred embodiment, lacing system 109 may be disposed in a substantially symmetric manner on middle portion 115. Furthermore, lacing system 109 may include medial lacing portion 110 associated with medial portion 106 and lateral lacing portion 111 associated with lateral portion 107.

In this embodiment, lacing system 109 includes lace 108 to secure a foot within upper 102. Generally, lace 108 may be configured with any length necessary to fasten upper 102. In addition, lace 108 may be configured in a particular shape visible in a cross section of lace 108. In some embodiments, lace 108 may include a substantially flat cross section. In other embodiments, lace 108 may be configured with a substantially rounded cross section.

An article of footwear may include provisions for increasing stability of a foot. In particular, an article may include provisions for increasing stability of a foot during lateral maneuvers. In some embodiments, the article may include provisions for stiffening a middle portion of the upper to help stabilize the foot within the upper in order to reduce the tendency of a foot to bend, roll, twist or otherwise move in an unstable manner. In a preferred embodiment, the upper may be associated with an arch wrap that is configured to help stiffen a middle portion of the upper.

In a preferred embodiment, article 100 may include arch wrap 150 to help provide stability and support for a foot. Preferably, arch wrap 150 may be disposed on middle portion 115 of upper 102. In some cases, a portion of arch wrap 150 may also extend to toe portion 113 as well.

Figure 3:
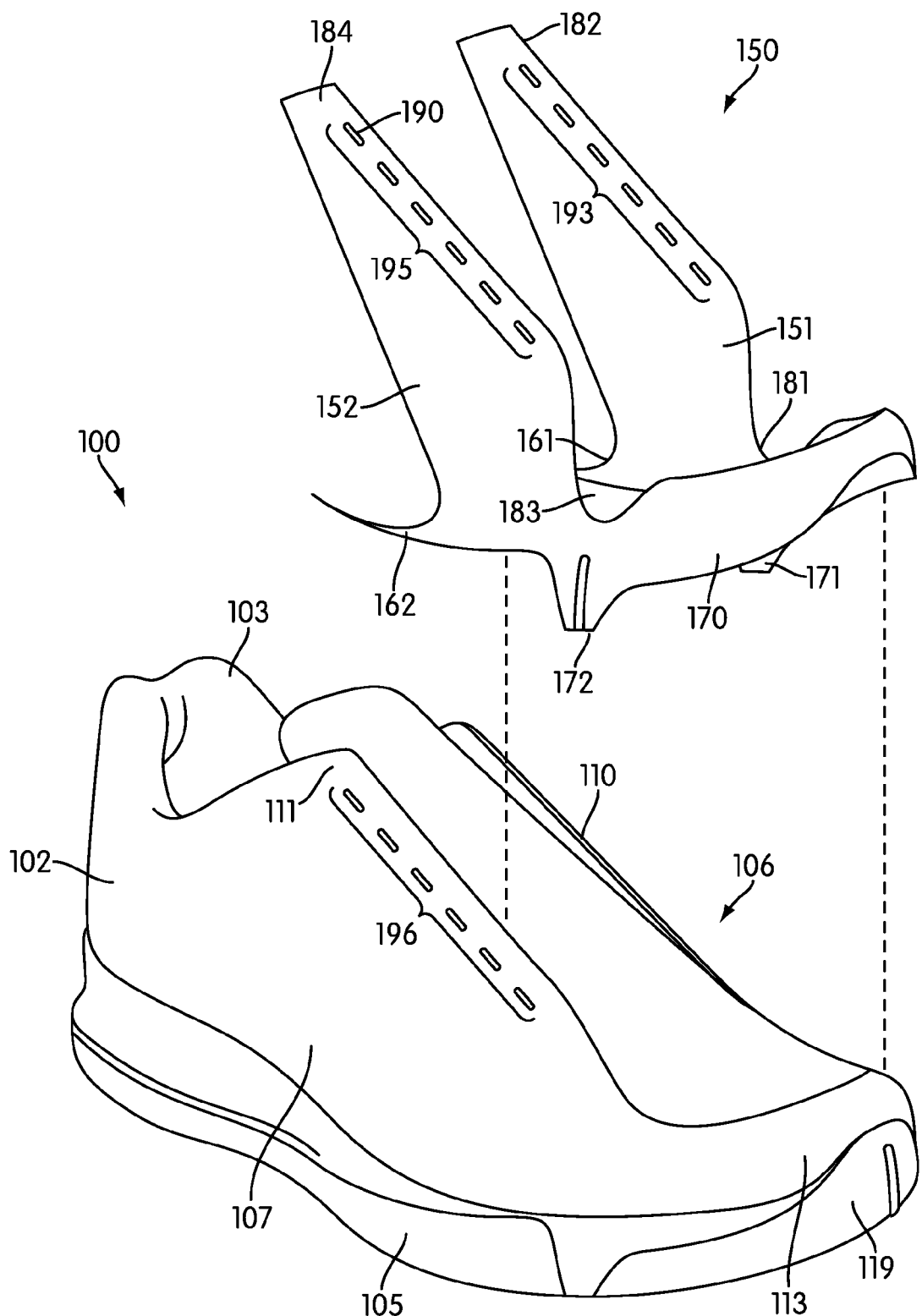
FIG. 3 is an exploded isometric view of a preferred embodiment of an article of footwear.

FIG. 3 is an exploded isometric view of a preferred embodiment of article 100. In particular, the shape of arch wrap 150 may be clearly visible in FIG. 3. Referring to FIGS. 1-3, in some embodiments, arch wrap 150 may include first extended portion 151 and second extended portion 152. Also, arch wrap 150 may include first rearward portion 161 and second rearward portion 162. Furthermore, arch wrap 150 may include forward portion 170. In some cases, forward portion 170 may further include first lower protrusion 171 and second lower protrusion 172.

In some embodiments, arch wrap 150 may be asymmetrical. In some cases, first extending portion 151 may be different in some way from second extending portion 152. In some embodiments, the two extending portions may have different lengths, they may have different sizes, or they may be different shapes. Arch wrap 150 can function even when first extending portion 151 is different in some way from second extending portion 152. In some embodiments, one of the extending portions, either first extending portion 151 or second extending portion 152 may be eliminated all together. Arch wrap 150 can also, in some embodiments, perform its intended function even when the two extending portions 151 and 152 are highly dissimilar, and even when one of the extending portions is completely eliminated.

As previously discussed, arch wrap 150 may be associated with middle portion 115. In this embodiment, first extended portion 151 may be associated with medial portion 106 of middle portion 115. In this preferred embodiment, first extended portion 151 may extend between toe portion 113 of upper 102 and entry hole 103. In particular, lower end portion 181 of first extended portion 151 may be disposed adjacent to toe portion 113. Likewise, upper end portion 182 of first extended portion 151 may be disposed adjacent to entry hole 103.

Second extended portion 152 may be associated with lateral portion 107 of middle portion 115. In this preferred embodiment, second extended portion 152 may extend between toe portion 113 of upper 102 and entry hole 103. In particular, lower end portion 183 of second extended portion 152 may be disposed adjacent to toe portion 113. Likewise, upper end portion 184 of second extended portion 152 may be disposed adjacent to entry hole 103.

Furthermore, first rearward portion 161 and second rearward portion 162 may also be associated with medial portion 106 and lateral portion 107, respectively. In some cases, first rearward portion 161 may extend from middle portion 115 towards sole system 105. Likewise, second rearward portion 162 may also extend from middle portion 115 towards sole system 105.

In some embodiments, forward portion 170 may be associated with toe portion 113 of upper 102. In some cases, forward portion 170 may be disposed adjacent to toe portion 119 of sole system 105. In other cases, forward portion 170 may be spaced apart from toe portion 119 of sole system 105. In this preferred embodiment, forward portion 170 may be configured to contact toe portion 119 of sole system 105. Furthermore, in some cases, first lower protrusion 171 and second lower protrusion 172 may extend through a portion of toe portion 119 of sole system 105. In other words, first lower protrusion 171 and second lower protrusion 172 may overlap with sole system 105 in some embodiments.

In different embodiments, the shapes and sizes of various portions of an arch wrap can vary. Generally, first extended portion 151 and second extended portion 152 can be associated with any shapes. Examples of different shapes include, but are not limited to square shapes, rectangular shapes, elliptical shapes, triangular shapes, regular shapes, irregular shapes as well as other types of shapes. In this preferred embodiment, first extended portion 151 and second extended portion 152 each have an approximately rectangular shape. Although first extended portion 151 and second extended portion 152 have substantially similar shapes in the current embodiment, in other embodiments, first extended portion 151 and second extended portion 152 could have different shapes.

Generally, first rearward portion 161 and second rearward portion 162 may also be associated with any shapes, including any of the shapes discussed above. In this preferred embodiment, first rearward portion 161 and second rearward portion 162 may be associated with approximately triangular shapes. However, in other embodiments, first rearward portion 161 and second rearward portion 162 could also have different shapes from one another.

Arch wrap 150 may include provisions for stiffening middle portion 115 of upper 102. In some embodiments, arch wrap 150 may be stiffer than upper 102. For example, in some cases, arch wrap 150 could be made of a substantially rigid plastic that is much stiffer than a fabric material used in making upper 102. In other cases, arch wrap 150 may be made of a similar material as upper 102, but arch wrap 150 may have a substantially greater thickness than upper 102 in order to increase the stiffness of arch wrap 150. With this arrangement, middle portion 115 may be prevented from deforming as much as other portions of upper 102 as upper 102 experiences various stresses during use.

An arch wrap may include provisions for associating with a lacing system of an upper. In such embodiments, as a lacing system is fastened, the arch wrap may be tightened against a midfoot to increase support to the midfoot. In a preferred embodiment, extended portions of an arch wrap may be co-extensive with portions of a lacing system.

In some embodiments, first extended portion 151 may be associated with medial lacing portion 110. In particular, first extended portion 151 may be co-extensive with a portion of medial lacing portion 110. Furthermore, second extended portion 152 may be associated with lateral lacing portion 111. In particular, second extended portion 152 may be co-extensive with a portion of lateral lacing portion 111. With this arrangement, first extended portion 151 and second extended portion 152 may be tightened against a midfoot as medial lacing portion 110 and lateral lacing portion 111 are fastened together with lace 108.

Figure 4:
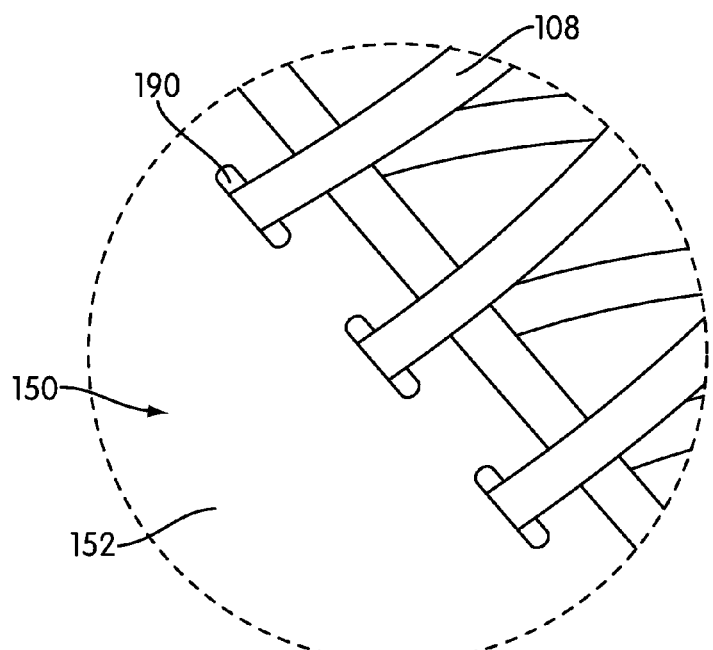
FIG. 4 is an enlarged view of a preferred embodiment of a portion of a lacing system for an article of footwear.

In embodiments where an arch wrap is associated with a lacing system, the arch wrap can include provisions for receiving a lace to help maintain the arch wrap in a tightened position during use. Referring to FIG. 4, arch wrap 150 may be provided with eyelets 190. Generally, eyelets 190 may be disposed in any portion of arch wrap 150. In a preferred embodiment, eyelets 190 may be disposed on first extended portion 151 and second extended portion 152 (see FIG. 3).

In some embodiments, eyelets 190 may be configured to align with eyelets of upper 102, as seen in FIG. 3. In particular, first extended portion 151 can be provided with first eyelet set 193 that is configured to align with an upper eyelet set of upper 102. Likewise, second extended portion 152 can be provided with second eyelet set 195 that is configured to align with second upper eyelet set 196 of upper 102. This arrangement preferably allows first extended portion 151 to be substantially integrated with medial lacing portion 110 and second extended portion 152 to be substantially integrated with lateral lacing portion 111.

In different embodiments, the number of eyelets disposed on an arch wrap may vary. In some cases, the arch wrap can include a single eyelet. In other cases, the arch wrap can include two or more eyelets. In a preferred embodiment, the arch wrap can include a set of eyelets that are in a one to one correspondence with eyelets in an upper.

Although the current embodiment includes an arch wrap with eyelets, in other embodiments, an arch wrap may not include any eyelets. Additionally, in other embodiments, an upper may not include eyelets. Instead, in these other embodiments, eyelets may be provided only in the arch wrap.

Generally, an arch wrap can be associated with an upper in any manner. In some cases, the arch wrap may be attached to an outer surface the upper. In other cases, the arch wrap may be attached to an interior surface of the upper. In still other cases, the arch wrap may be attached to between an outer surface of the upper and an interior surface of the upper. Furthermore, the method of attaching the arch wrap can include stitching, adhesives, as well as other methods known in the art.

In previous designs, an arch wrap may be applied to a portion of an upper in a generally vertical manner. In other words, the arch wrap may be oriented in a substantially perpendicular direction with a sole system. In such designs, the arch wrap may only be disposed adjacent to a small portion of a foot. This may inhibit the ability of the arch wrap to facilitate stability over the whole midfoot.

Preferably, an arch wrap includes provisions for facilitating stability over an entire midfoot. In some embodiments, the arch wrap can include extended portions that are angled. In a preferred embodiment, the extended portions are angled to follow the natural contour of the midfoot.

Figure 5:
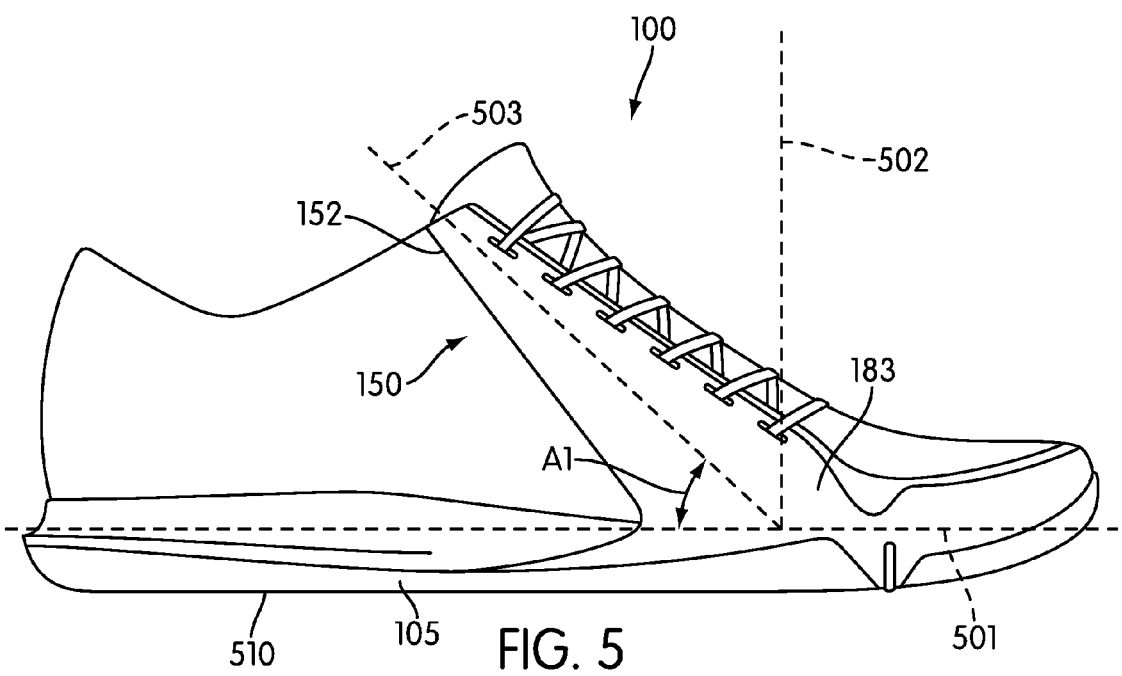
FIG. 5 is a side view of a preferred embodiment of an article of footwear.

FIG. 5 illustrates a side view of a preferred embodiment of article 100. Referring to FIG. 5, arch wrap 150 is configured with second extended portion 152 oriented across a majority of middle portion 115 to provide stability for the entire midfoot. In particular, second extended portion 152 is substantially angled with respect to sole system 105.

In this embodiment, article 100 is associated with first axis 501 that is generally parallel with lower surface 510 of sole system 105. First axis 501 may be oriented in a generally longitudinal direction. The term "longitudinal direction" as used throughout this detailed description and in the claims refers to a direction extending a length of article 100. Likewise, article 100 is associated with second axis 502 that is generally perpendicular to first axis 501. Preferably, second axis 502 and first axis 501 generally intersect around lower end portion 183 of second extended portion 152.

Second extended portion 152 may be associated with third axis 503. Generally, third axis 503 intersects first axis 501 and second axis 502 at an origin of first axis 501 and second axis 502. Furthermore, third axis 503 extends through the length of second extended portion 152 and approximately bisects second extended portion 152.

As seen in FIG. 5, third axis 503 is angled with respect to first axis 501 by an angle A1. In other words, second extended portion 152, which is substantially parallel with third axis 503, is angled from sole system 105 by angle A1. Although only second extended portion 152 is visible in FIG. 5, it should be assumed that first extended portion 151 may be angled in a substantially similar manner with respect to sole system 105.

In different embodiments, the value of angle A1 may vary. In some embodiments, angle A1 may vary in a range between 0 and 90 degrees. In other embodiments, angle A1 may vary in a range between 30 and 60 degrees. In a preferred embodiment, angle A1 may vary in a range between 40 and 55 degrees. With this preferred orientation, arch wrap 150 may be configured to follow the shape of a midfoot within upper 102.

Generally, each component of article of footwear 100 may be constructed of any material. Sole system 105 may be constructed from any suitable material, including but not limited to elastomers, siloxanes, natural rubber, other synthetic rubbers, aluminum, steel, natural leather, synthetic leather, or plastics. Also, upper 102 may be made from any suitable material, including but not limited to, for example, nylon, natural leather, synthetic leather, natural rubber, or synthetic rubber.

In different embodiments, arch wrap 150 can be made of different materials. Examples of different materials that can be used include, but are not limited to elastomers, siloxanes, natural rubber, other synthetic rubbers, aluminum, steel, natural leather, synthetic leather, plastics, nylon, natural leather, synthetic leather as well as other types of materials. In some cases, arch wrap 150 can be made of a substantially stiff or rigid material in order to facilitate support to a midfoot. By selecting different types of materials for arch wrap 150, the degree of stiffness of arch wrap 150 can be fine tuned to accommodate the needs of a particular article of footwear.

Generally, lace 108 may comprise any material including, but not limited to leather, cotton, jute, hemp, or synthetic fibers. Additionally, lace 108 may be coated with a material to increase friction in order to keep lace 108 fastened. In some cases, lace 108 may include elastic portions. Also, in some cases, one or more ends of lace 108 may be configured with aglets to make threading lace 108 easier.

Figure 6:
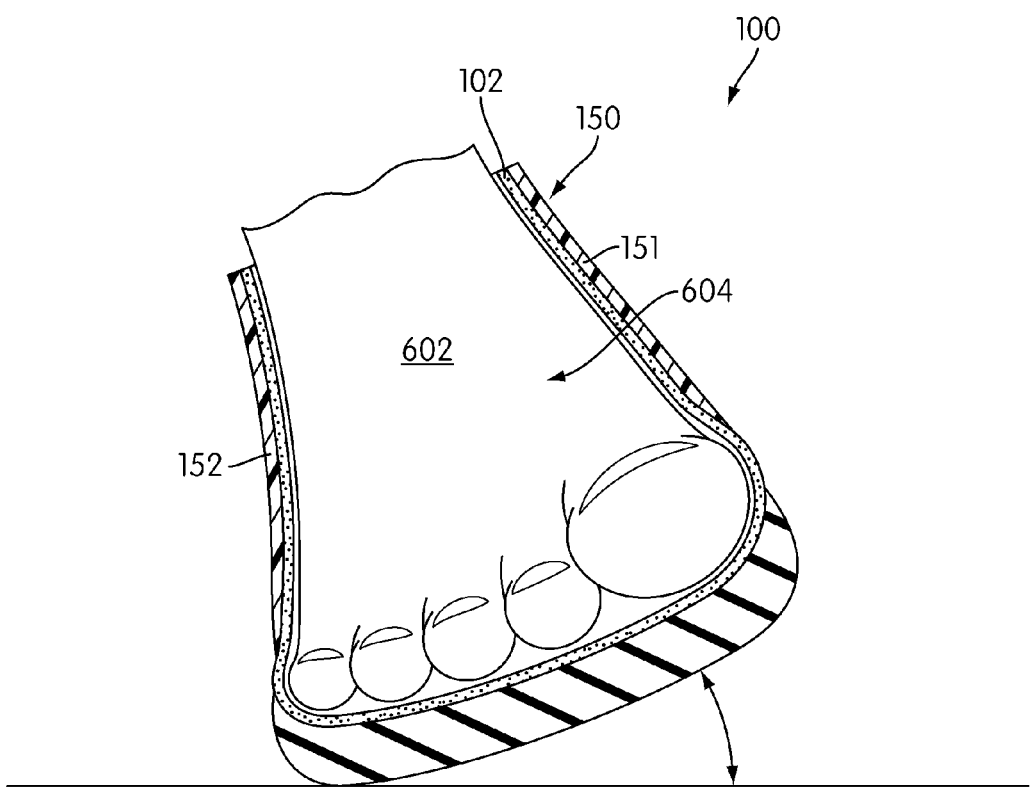
FIG. 6 is a schematic cross sectional view of a preferred embodiment of an article of footwear tilting to a lateral side.

FIG. 6 illustrates a schematic cross sectional view of a preferred embodiment of an article of footwear with an arch wrap. Referring to FIG. 6, article 100 includes upper 102 and arch wrap 150. As previously discussed, arch wrap 150 further includes first extended portion 151 and second extended portion 152. As article 100 rolls slightly to a lateral side of article 100, foot 602 is preferably prevented from bending within upper 102 due to the presence of arch wrap 150. In particular, first extended portion 151 and second extended portion 152 wrap tightly against a majority of midfoot 604 of foot 602 in order to maintain foot 602 in a generally straight position. With this arrangement, arch wrap 150 may provide increased support for midfoot 604 of foot 602 during use of article 100.

Figure 7:
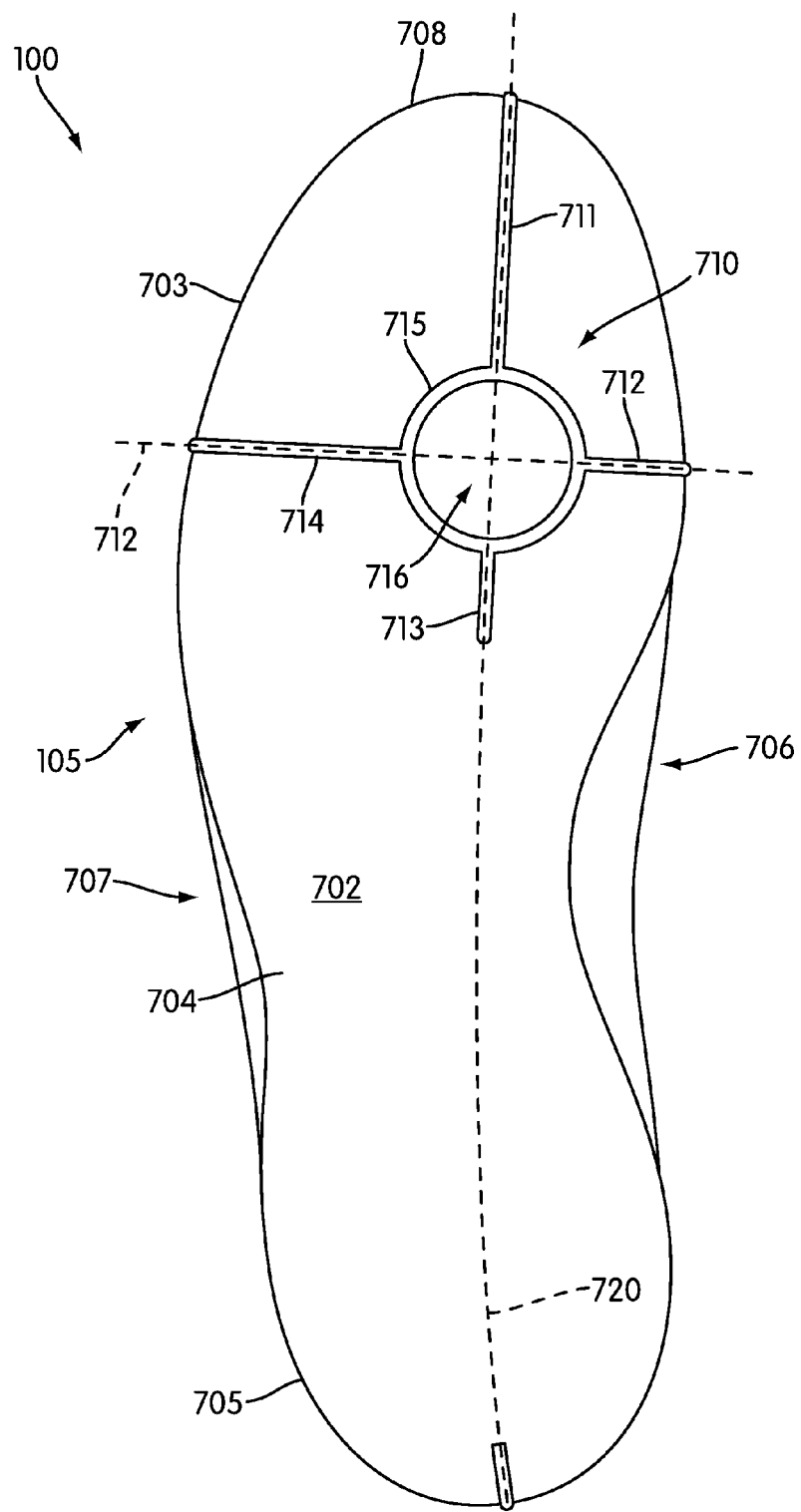
FIG. 7 is a bottom view of a preferred embodiment of a sole system.

FIG. 7 illustrates a preferred embodiment of a lower surface of a sole system. Referring to FIG. 7, sole system 105 of article 100 may include lower surface 702. In some cases, lower surface 702 may be associated with an outsole. In other cases, lower surface 702 may be associated with a lower surface of a midsole. In a preferred embodiment, lower surface 702 is associated with an outsole of sole system 105.

Generally, lower surface 702 can be provided with provisions to increase traction with a ground surface. For example, in some embodiments, lower surface 702 can be provided with one or more tread elements. In other embodiments, lower surface 702 can include one or more cleats that are configured to penetrate through a ground surface such as grass. For purposes of clarity, lower surface 702 is illustrated here as generally flat, however it should be understood that in other embodiments lower surface 702 can include any combination of tread elements, cleats and/or other types of tread patterns to help increase traction with a ground surface.

Generally, sole system 105 may be associated with one or more portions. In this embodiment, sole system 105 may include forefoot portion 703, arch portion 704 and heel portion 705. In some cases, forefoot portion 703 may further include toe portion 708. Sole system 105 may also include medial portion 706 and lateral portion 707.

In order to effectively train an athlete, a trainer may be required to accurately study the positioning of a foot of the athlete during various athletic drills. In some cases, a trainer may film the foot of an athlete as the athlete performs various athletic drills. By analyzing the film at a later time, the trainer may be able to determine the location of one or more portions of a foot in order to study the precise movements of the athlete throughout the drill.

In embodiments where the motions of the foot of an athlete may be accurately studied, an article of footwear may include provisions to help a trainer accurately determine the location of one or more portions of a foot of the athlete. In some embodiments, one or more markings may be provided on a sole system of the article of footwear in order to enable the trainer to properly locate one or more portions of the foot. In a preferred embodiment, a set of markings may be used in cooperation with one another to help accurately locate one or more portions of a foot.

Referring to FIG. 7, sole system 105 may be provided with marking system 710. Marking system 710 may comprise first marking 711, second marking 712, third marking 713 and fourth marking 714. Furthermore, marking system 710 may also include central marking portion 715.

In different embodiments, the location of marking system 710 may vary. In some embodiments, marking system 710 may be disposed on forefoot portion 703 of sole system 105. In other embodiments, marking system 710 may be disposed on arch portion 704 of sole system 105. In still other embodiments, marking system 710 may be disposed on heel portion 705 of sole system 105. In this preferred embodiment, marking system 710 is disposed in forefoot portion 703 and extends to heel portion 705 as well. In particular, third marking 713 extends through forefoot portion 703 and heel portion 705.

Generally, marking system 710 may be disposed anywhere on forefoot portion 703. In some cases, central marking portion 715 may be associated with a predetermined portion of forefoot portion 703 that is adjacent to a particular feature of a foot. For example, in the current embodiment, central marking portion 715 is disposed in ball portion 716 of forefoot portion 703. Preferably, ball portion 716 is a location in forefoot portion 703 that is disposed adjacent to the ball of a foot during the use of article 100. In other words, ball portion 716 is disposed just beneath the ball of the foot of an athlete. With this arrangement, the location of the ball of the foot of an athlete can be accurately determined by locating central marking portion 715 on lower surface 702.

In other embodiments, marking system 710 could be used for locating any predetermined portion of a sole system that corresponds to a particular location of a foot. Although central marking portion 715 is associated with the ball of a foot in the current embodiment, it should be understood that central marking portion 715 could be associated with other features of a foot in other embodiments. For example, in another embodiment, central marking portion 715 could be disposed in arch portion 704 to help a trainer accurately locate the arch of a foot during a training session. Likewise, in another embodiment, central marking portion 715 could be disposed in heel portion 705 to help a trainer accurately locate the heel of a foot during a training session. In still other embodiments, central marking portion 715 could associated with one or more bones in the feet, including, but not limited to, phalanges, metatarsals, cuniforms and the calcaneus, as well as other bones. In still other embodiments, central marking portion 715 could be associated with a particular muscle in the foot.

When a trainer is monitoring the movement of a foot of an athlete, lower surface 702 may be oriented to face the ground surface and therefore may not be visible to an observer. Preferably, first marking 711, second marking 712, third marking 713 and fourth marking 714 may be arranged to help the trainer in accurately detecting the location of central marking portion 715 during a training exercise. In a preferred embodiment, marking system 710 may be arranged in a crosshair pattern to assist in locating a particular location on sole system 105 and the associated portion of the foot.

In this embodiment, first marking 711 may extend from central marking portion 715 towards toe portion 708 of forefoot portion 703. Likewise, third marking 713 may extend from central marking portion 715 towards heel portion 705. In a preferred embodiment, first marking 711 and third marking 713 may be substantially co-linear. In particular, first marking 711 and third marking 713 may be aligned with longitudinal axis 720. The term "longitudinal axis" as used throughout this detailed description and in the claims refers to an axis that extends in a longitudinal direction, which is a direction extending the length of sole system 105.

In a similar manner, second marking 712 may extend from central marking portion 715 towards medial portion 706. Likewise, fourth marking 714 may extend from central marking portion 715 towards lateral portion 707. In a preferred embodiment, second marking 712 and fourth marking 714 may be substantially co-linear. In particular, second marking 712 and fourth marking 714 may be aligned with lateral axis 721. The term "lateral axis" as used throughout this detailed description and in the claims refers to an axis that extends in a lateral direction, which is a direction running a width of sole system 105.

Using this preferred arrangement, marking system 710 may be used to implicitly define longitudinal axis 720 and lateral axis 721. Furthermore, longitudinal axis 720 and lateral axis 721 are configured to intersect approximately at ball portion 716. With this configuration for marking system 710, a trainer may accurately determine the location of ball portion 716 even when central marking portion 715 is not directly visible. Instead, by knowing the locations of at least two markings of marking system 710, the trainer can use this information to determine the location of central marking portion 715 by determining the intersection point of longitudinal axis 720 and lateral axis 721 that are associated with the markings.

Figure 8:
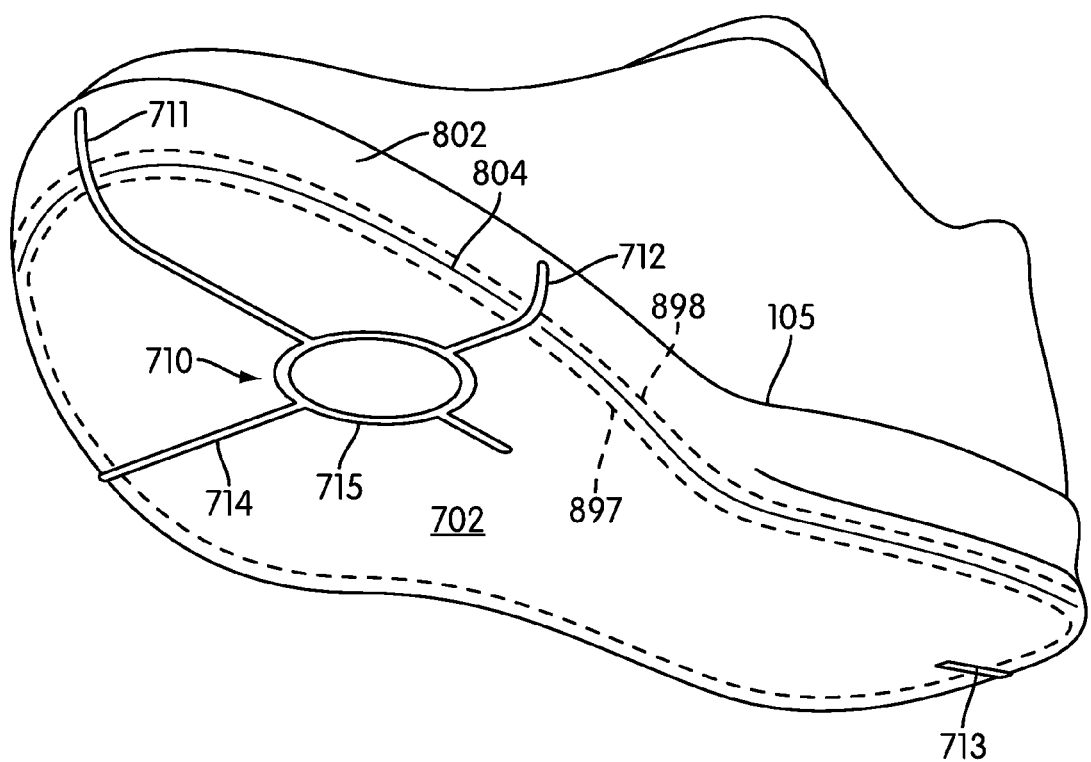
FIG. 8 is a front isometric view of a preferred embodiment of a sole system.
Figure 9:
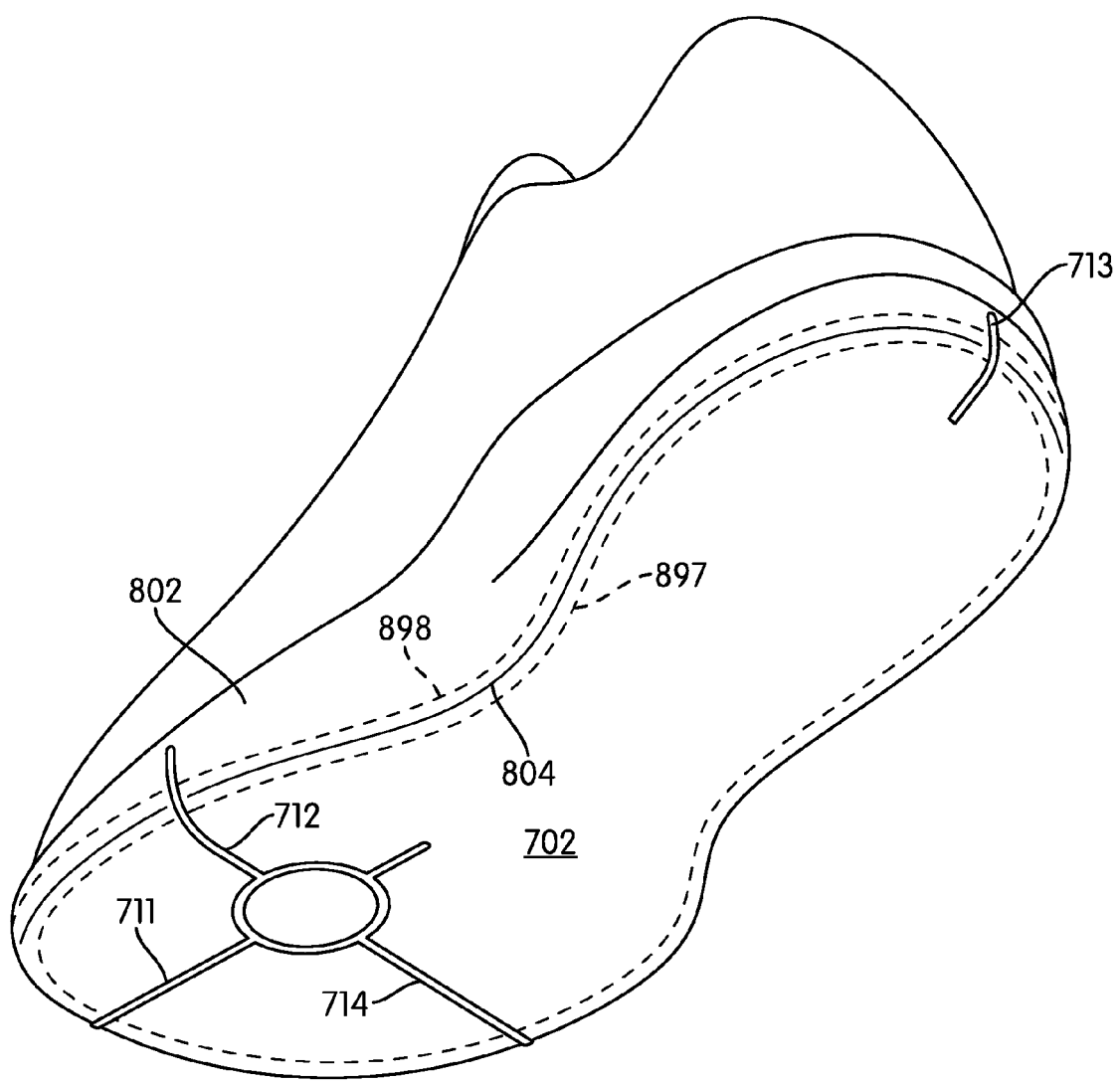
FIG. 9 is a rear isometric view of a preferred embodiment of a sole system.

In embodiments where a trainer can only view edges of a sole system, the sole system can be provided with markings that extend to the edges to facilitate accurately locating one or more portions of a foot. FIG. 8 is a front isometric view of a preferred embodiment of a sole system from below. FIG. 9 is a rear isometric view of a preferred embodiment of a sole system from below. Referring to FIGS. 8 and 9, sole system 105 may be associated with outer peripheral portion 802. Preferably, outer peripheral portion 802 is a side edge of sole system 105. Sole system 105 may also include corner portion 804 that is disposed between outer peripheral portion 802 and lower surface 702. For purposes of illustration, the boundaries of corner portion 804 are indicated at first boundary 897 and second boundary 898. However, it should be understood that the width of corner portion 804 is not restricted to a particular size.

In some embodiments, each marking of marking system 710 may be configured to extend from lower surface 702 to outer peripheral portion 802. For example, first marking 711 may extend from lower surface 702, through corner portion 804 and into outer peripheral portion 802. In a similar manner, second marking 712, third marking 713 and fourth marking 714 may also extend from lower surface 702 through corner portion 804 and into outer peripheral portion 802. With this arrangement each marking may be partially visible on outer peripheral portion 802 and corner portion 804. In particular, each marking is partially visible even as lower surface 702 is disposed against a ground surface.

In different embodiments, the shape of each marking of a marking system can vary. In some embodiments, each marking can be a straight line with a generally constant thickness. In other embodiments, each marking can be a straight line with varying thickness. In still other embodiments, each marking can have another shape, including, but not limited to, triangular shapes, rectangular shapes, elliptical shapes, regular shapes, irregular shapes as well as other types of shapes.

In different embodiments, the size and shape of a central marking portion can vary. In some embodiments, the central marking portion can have a single point-like shape that corresponds to the intersection of two or more markings. In other embodiments, the central marking portion can have a ring like shape. In still other embodiments, the central marking portion can have a disc-like shape. In still other embodiments, the central marking portion could have any shape including, but not limited to triangular shapes, rectangular shapes, elliptical shapes, regular shapes, irregular shapes as well as other types of shapes. In a preferred embodiment, the central marking portion may have a ring like shape.

A marking system can be applied to a sole system in any manner. For example, in one embodiment, a marking system may be painted onto a sole system using a durable paint. In another example, a marking system can comprise portions of a distinct material that are applied to the sole system using an adhesive of some kind. Examples of materials that could be used for a marking system include, but are not limited to, plastic, rubber, leather, natural fibers, synthetic fibers, metal as well as other types of materials. In still another example, a marking system may be formed during a molding process by using a distinct color for the regions of the sole system associated with the markings.

In embodiments including both an arch wrap and a marking system, an article can be provided with provisions for aligning lateral markings with the arch wrap. In some embodiments, one or more lateral markings may extend into portions of the arch wrap. This arrangement can be useful in cases where a trainer wants to accurately locate one or more portions of the arch wrap while monitoring an athlete.

Figure 10:
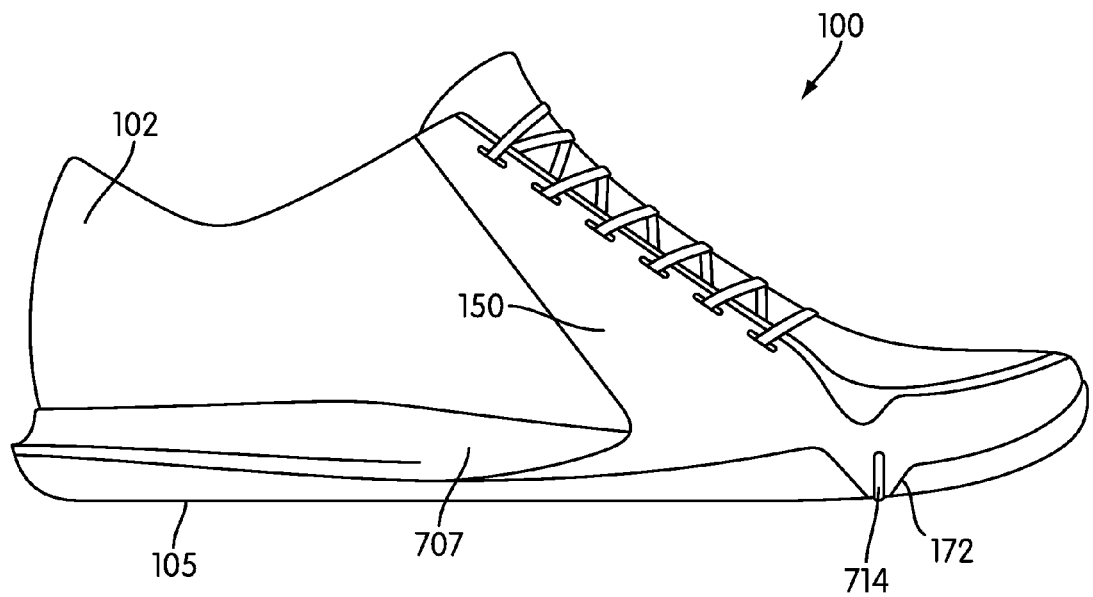
FIG. 10 is a side view of a preferred embodiment of an article of footwear.
Figure 11:
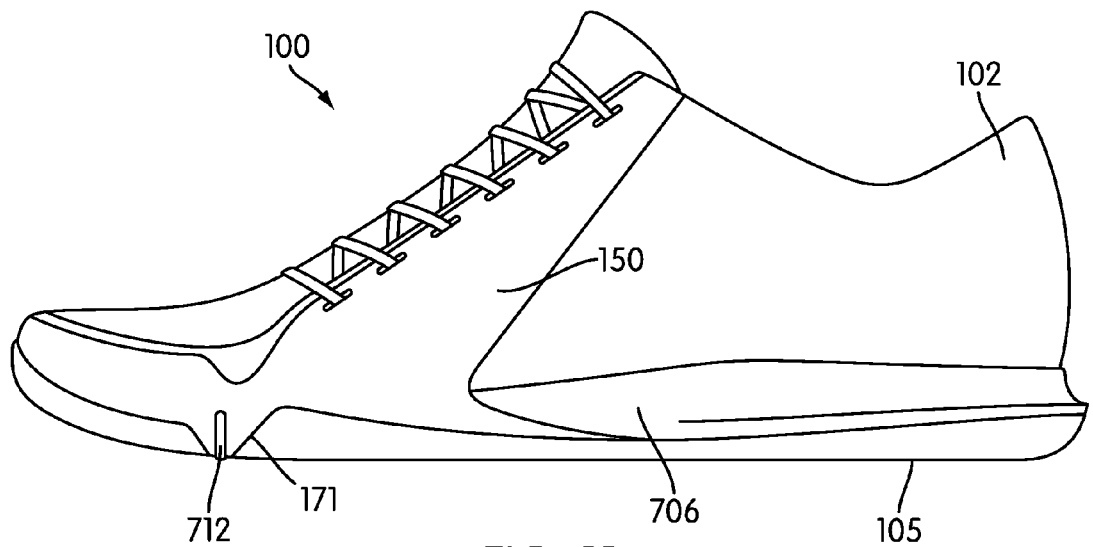
FIG. 11 is a side view of a preferred embodiment of an article of footwear.

FIGS. 10 and 11 illustrate side lateral and medial views of a preferred embodiment of article 100, respectively. Referring to FIGS. 10 and 11, fourth marking 714 is partially visible on lateral portion 707. In particular, fourth marking 714 is configured to extend into second lower protrusion 172 of arch wrap 150, which overlaps with outer peripheral portion 802. Likewise, second marking 712 is partially visible on medial portion 706. In particular, second marking 712 is configured to extend into first lower protrusion 171 of arch wrap 150, which overlaps with outer peripheral portion 802. With this preferred arrangement, a trainer may also accurately locate one or more portions of arch wrap 150 using second marking 712 and fourth marking 714.

Figure 12:
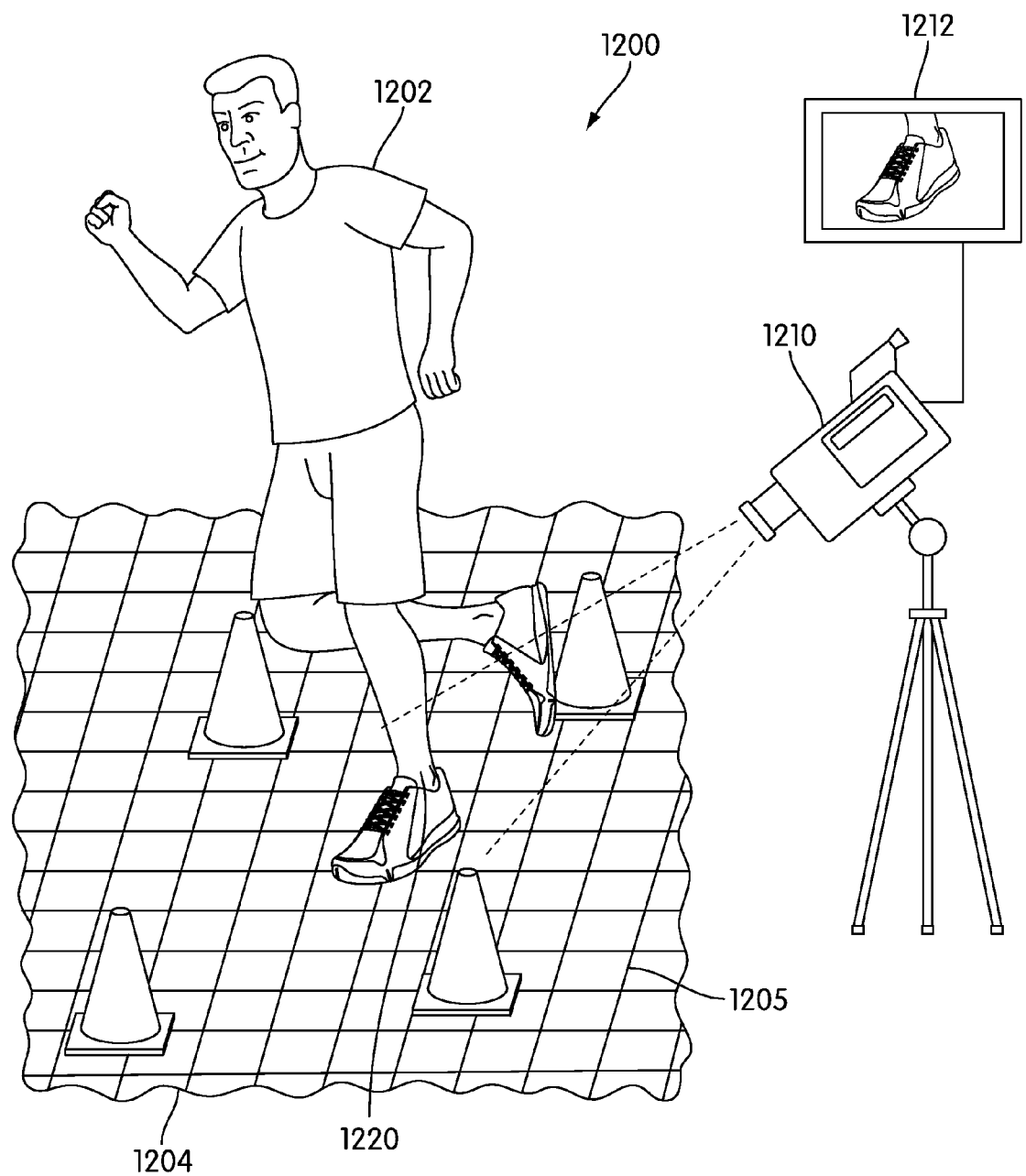
FIG. 12 is a schematic view of an exemplary embodiment of a training system.
Figure 13:
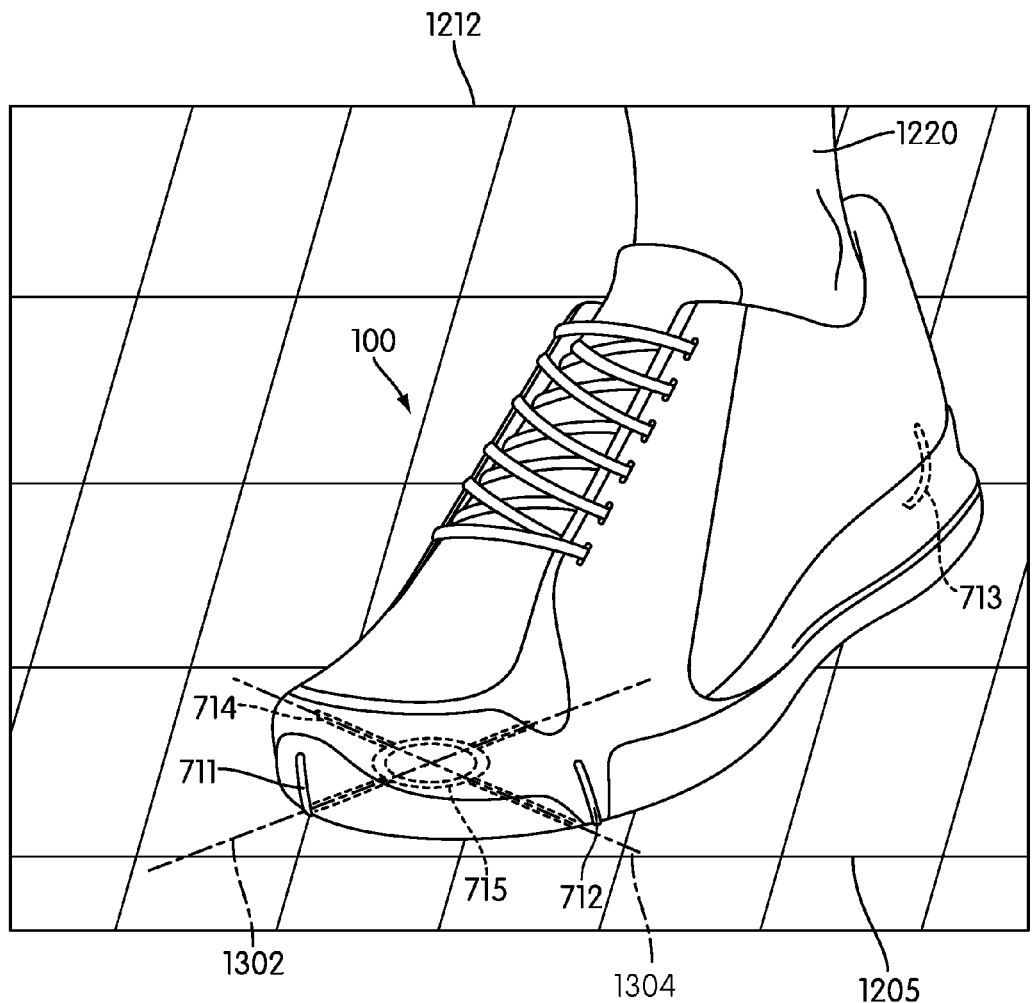
FIG. 13 is an enlarged view of an exemplary embodiment of a single frame of movement of a foot of an athlete displayed on a video display system.

FIGS. 12 and 13 are intended to illustrate an exemplary embodiment of a training system for an athlete. Referring to FIG. 12, training system 1200 may be associated with practice field 1204. The term "practice field", as used throughout this detailed description, refers to any type of field, court, or generally open space that may be used for training activities. Examples of practice fields include, but are not limited to, football fields, soccer pitches or fields, lacrosse fields, basketball courts, as well as other types of fields and/or courts. Additionally, any open space that may be used for training activities such as those described throughout this detailed description may also be considered a practice field.

Preferably, training system 1200 may also include athlete 1202. The term "athlete" is intended to include both professional athletes and amateur athletes. Generally, athlete 1202 may be any person wishing to take part in an athletic training activity. Therefore, the term "athlete", as used throughout this detailed discussion and in the claims, refers to any user of training system 1200.

Preferably, an article of footwear used with training system 1200 includes provisions for training an athlete with respect to various athletic skills that are important for a strong performance in many sports. Examples of these athletic skills include, but are not limited to stride length, forefoot planting technique, linear speed, lateral speed, left turning speed, right turning speed, starting acceleration, mid-stride acceleration, deceleration as well as other capabilities. For example, a running back in football must have good lateral speed in order to avoid tackles. Therefore, it may be important to have a training system with special emphasis placed on one or more of these athletic skills.

In some cases, practice field 1204 may include provisions to assist in accurately locating athlete 1202 on practice field 1204. For example, in this embodiment, practice field 1204 includes grid 1205. Generally, grid 1205 can be any type of grid. Furthermore, grid 1205 can include any size spacing. In this preferred embodiment, the size of grid 1205 can be selected to allow for accurate measurements of the locations of a portion of a foot during a training session.

In some embodiments, training system 1200 may include provisions to monitor athlete 1202 during one or more training activities. In this embodiment, training system 1200 may include monitoring device 1210. In some cases, monitoring device 1210 may be a camera. In other cases, monitoring device 1210 may be a video camera. In still other cases, monitoring device 1210 could be any type of device configured to measure movements of an athlete, especially the feet of an athlete. In this preferred embodiment, monitoring device 1210 may be a video camera that is configured to capture movements of the feet of an athlete during the training session.

Monitoring device 1210 may be associated with one or more provisions for receiving information about the performance of athlete 1202. In some cases, monitoring device 1210 may be in communication with a computer. The term "computer" refers to any device including a central processing unit, some kind of memory, a user interface and mechanisms for input/output. A computer can be a portable computer, for example, a laptop, notebook or Personal Data Assistant (PDA). A computer can include a database, generally residing in a mass storage device like a hard disk drive or an optical storage device. The term "computer" refers to the computing resources of a single computer, a portion of the computing resources of a single computer, and/or two or more computers in communication with one another, also any of these resources can be operated by one or more human users. In an exemplary embodiment, a computer includes a personal computer.

In a preferred embodiment, monitoring device 1210 may be in communication with a video display system. The term "video display system" as used throughout this detailed description and in the claims refers to any system that includes provisions for displaying one or more video images received from monitoring device 1210. Examples of various video display systems include, but are not limited to, digital video disc (DVD) players, video cassette recorders (VCRs), navigational systems, game consoles, television tuners, cable boxes, digital video recorders (DVRs), video cameras, digital cameras, computers, karaoke machines as well as any other type of electrical device that can produce video output that may be displayed on a screen of some kind.

Preferably, monitoring device 1210 may be configured to communicate with video display system 1212. In some embodiments, monitoring device 1210 may communicate with video display system 1212 via a wireless network, including but not limited to any broadband wireless access network or a high bandwidth packet switched network using, for example, any one of the following standards: IEEE 802.11a, IEEE 802.11b, IEEE 802.11g, commonly referred to as WiFi, and/or IEEE 802.16a, referred to as WiMAX. Monitoring device 1210 may also communicate with video display system 1212 via the Bluetooth protocol.

Referring to FIGS. 12 and 13, as athlete 1202 moves on practice field 1204, monitoring device 1210 may be configured to record the movements of athlete 1202. In particular, in some cases, monitoring device 1210 may be configured to record movements of one or more feet of athlete 1202. Preferably, monitoring device 1210 is configured to transmit a signal to video display system 1212 that includes one or more images of athlete 1202. In some cases, monitoring device 1210 may transmit live images to video display system 1212 so that the images can be viewed in real time. In other cases, monitoring device 1210 may record athlete 1202 during a training session and later transmit the images to video display system 1212 for a trainer to view at a later time.

Referring to FIG. 13, monitoring device 1210 has captured a single frame of the movement of foot 1220 of athlete 1202, which is displayed on video display system 1212. At this point, a trainer may study this frame, or a sequence of frames, in order to accurately determine the motion of foot 1220 during a portion of the training session. For example, the trainer may wish to determine the exact location of the ball of foot 1220 during a particular athletic maneuver in order to determine if athlete 1202 is performing the maneuver correctly. Preferably, training system 1200 includes provisions for assisting a trainer in accurately determining the location of one or more portions of a foot, such as the ball of a foot.

In this embodiment, athlete 1202 is wearing article 100. As previously discussed, article 100 may be provided with marking system 710. Furthermore, marking system 710 includes first marking 711, second marking 712, third marking 713, fourth marking 714 and central marking portion 715. For purposes of illustration, third marking 713, fourth marking 714 and central marking portion 715 are shown in phantom in this embodiment. However, only a portion of first marking 711 and second marking 712 may be visible on sole system 105. In other words, when viewing the image on video display system 1212, a trainer may only see first marking 711 and second marking 712. In particular, the remaining markings as well as the exact location of ball portion 716 are obscured by the top of article 100.

In order to accurately determine the location of ball portion 716, a trainer may utilize marking system 710. Preferably, the trainer may determine the location of first marking 711 by inspecting the image of article 100. Also, the trainer may determine the location of second marking 712 in a similar manner. At this point, the trainer may associate longitudinal axis 1302 with first marking 711 and lateral axis 1304 with second marking 712. In some cases, longitudinal axis 1302 and lateral axis 1304 can be traced out onto video display system 1212 using a graphical illustrator of some kind. For example, if video display system 1212 is connected to a computer, the trainer can use a graphical program to overlay longitudinal axis 1302 and lateral axis 1304 on the image of article 100. In other cases, a trainer can mentally estimate the locations of longitudinal axis 1302 and lateral axis 1304. Preferably, the trainer may then proceed to determine where longitudinal axis 1302 and lateral axis 1304 may intersect. The point of intersection then allows the trainer to identify the location of ball portion 716. Furthermore, using grid 1205, the trainer can accurately determine the location of ball portion 716 with respect to practice field 1204.

In some cases, a trainer can repeat these steps to determine the location of ball portion 716 throughout a particular time interval of the training session. For example, by monitoring a sequence of images corresponding to the location of foot 1220, the trainer may use marking system 710 to accurately determine the location of a ball of foot 1220 throughout the sequence. Using this information, the trainer may determine the exact travel path of the ball of foot 1220. This information can be useful in analyzing one or more physical characteristics of the athlete, including, but not limited to, stride length, forefoot planting technique, linear speed, lateral speed, left turning speed, right turning speed, starting acceleration, midstride acceleration, deceleration as well as other capabilities.

Although the current embodiment discusses a single foot with a single article of footwear, it should be understood that training system 1200 can be used to monitor and accurately study both feet of an athlete including an associated pair of footwear.

Although the current embodiment is used for determining the accurate location of a ball of a foot, in other embodiments, a marking system for an article of footwear can be used to accurately locate other portions of a foot, such as a toe portion, an arch portion, a heel portion, as well as other portions. Furthermore, in some embodiments, multiple marking systems can be used on an article of footwear for simultaneous location of multiple portions of the foot.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

We claim:

1. An article of footwear, comprising:
an upper having a toe portion, a heel portion disposed opposite the toe portion, a middle portion disposed between the toe portion and the heel portion, a lateral side, and a medial side;
a sole system associated with the upper;
a first axis substantially parallel with the sole system and oriented in a longitudinal direction of the article of footwear;
an arch wrap configured to be disposed adjacent to a middle portion of the upper; and
the arch wrap including a first extended portion extending from the toe portion at one of the lateral side and the medial side, wherein a second axis extends through the entire length of the first extended portion and approximately bisects the first extended portion, the second axis extending upwardly and rearwardly at an angle with respect to the first axis.

2. The article of footwear according to claim 1, wherein the second axis is angled from the first axis at an angle A1 ranging between about 10 degrees and about 80 degrees.

3. The article of footwear according to claim 2, wherein the angle A1 ranges between about 30 degrees and about 60 degrees.

4. The article of footwear according to claim 2, wherein the angle A1 ranges between about 40 degrees and about 55 degrees.

5. The article of footwear according to claim 1, wherein the arch wrap includes a rearward portion extending rearwardly from a lower end portion of the first extended portion.

6. The article of footwear according to claim 1, wherein the arch wrap includes a forward portion extending across the toe portion from a first end disposed on the medial side to a second end disposed on the lateral side.

7. The article of footwear according to claim 6, wherein the arch wrap includes a second extended portion extending from one of the first end and the second end of the forward portion, the second extended portion extending upwardly and rearwardly at an angle with respect to the first axis.

8. The article of footwear according to claim 7, wherein a third axis extends through the entire length of the second extended portion and approximately bisects the second extended portion, the second axis being angled from the first axis at a second angle A2, the second angle having a value in a range between about 0 degrees and about 90 degrees.

9. The article of footwear according to claim 8, wherein the angle A2 has a value in a range between about 30 degrees and about 60 degrees.

10. An article of footwear, comprising:
an upper having a toe portion, a heel portion disposed opposite the toe portion, a middle portion disposed between the toe portion and the heel portion, a lateral side, and a medial side, the upper including an entry hole configured to receive a foot of a wearer and a lacing system having a lateral lacing portion and a medial lacing portion;
a sole system associated with the upper;
an arch wrap configured to be disposed adjacent to a middle portion of the upper;
the arch wrap including a first extended portion extending in a straight line from the entry hole to a point on the toe portion of the sole system located on one of the lateral side and the medial side; and
wherein the first extended portion is co-extensive with one of the lateral lacing portion and the medial lacing portion.

11. The article of footwear according to claim 10, wherein the extended portion tapers from the toe portion to the entry hole.

12. The article of footwear according to claim 10, wherein the arch wrap includes a second extended portion extending in a straight line from the entry hole to a point on the toe portion located on one of the lateral side and the medial side.

13. The article of footwear according to claim 12, wherein the first extended portion is co-extensive with the medial lacing portion of the lacing system and the second extended portion is co-extensive with the lateral lacing portion of the lacing system.

14. The article of footwear according to claim 10, wherein the arch wrap includes a forward portion formed integrally as one piece with the first extended portion, the forward portion extending across the toe portion from a first end disposed on the medial side to a second end disposed on the lateral side and the first extended portion extending from one of the first end and the second end.

15. An article of footwear, comprising:
an upper having a toe portion, a heel portion disposed opposite the toe portion, a middle portion disposed between the toe portion and the heel portion, a lateral side, and a medial side, the upper including a lacing system having a first plurality of eyelets;
a sole system associated with the upper;
an arch wrap configured to be disposed adjacent to a middle portion of the upper;
the arch wrap including a first extended portion having a first region extending forwardly and downwardly from a bottom eyelet of the first plurality of eyelets to a point on the toe portion located on one of the lateral side and the medial side adjacent the sole system;
wherein the first extended portion includes a second region connected to the first region and having a second plurality of eyelets corresponding with the first plurality of eyelets of the upper, wherein the second plurality of eyelets are disposed in a straight line from a top eyelet of the second plurality of eyelets to a bottom eyelet of the second plurality of eyelets along an edge of the first extended portion and the second plurality of eyelets are configured to receive a lace of the lacing system; and
the arch wrap including a forward portion extending across the toe portion from a first end disposed on the medial side to a second end disposed on the lateral side, wherein the first extended portion extends from the bottom eyelet to one of the first end and the second end.

16. The article of footwear according to claim 15, wherein the forward portion and the extended portion are integrally formed as one piece.

17. The article of footwear according to claim 15, wherein the arch wrap includes a second extended portion extending forwardly and downwardly from a bottom eyelet of the first plurality of eyelets to a point on the toe portion located on one of the lateral side and the medial side adjacent the sole system.

18. The article of footwear according to claim 15, wherein the first extended portion tapers from the toe portion to an entry hole of the upper.

19. The article of footwear according to claim 15, wherein the first extended portion extends in a straight line from the toe portion of the upper to an entry hole of the upper.

20. The article of footwear according to claim 15, wherein a first axis is substantially parallel with the sole system and oriented in a longitudinal direction of the article of footwear and wherein a second axis extends through the length of the first extended portion and approximately bisects the first extended portion, the second axis being angled from the first axis at an angle A1 ranging between about 30 degrees and about 60 degrees.

* * * * *